United States Patent
Hatscher et al.

(10) Patent No.: US 8,680,350 B2
(45) Date of Patent: Mar. 25, 2014

(54) PROCESS FOR HYDROGENATING UNSATURATED HYDROCARBONS IN THE PRESENCE OF CATALYSTS CONTAINING COPPER AND ZINC

(75) Inventors: Stephan Hatscher, Syke (DE); Michael Hesse, Worms (DE)

(73) Assignee: BASF SE, Ludwigshafen (DE)

( * ) Notice: Subject to any disclaimer, the term of this patent is extended or adjusted under 35 U.S.C. 154(b) by 752 days.

(21) Appl. No.: 12/374,191

(22) PCT Filed: Jul. 5, 2007

(86) PCT No.: PCT/EP2007/056858
§ 371 (c)(1),
(2), (4) Date: Jan. 16, 2009

(87) PCT Pub. No.: WO2008/009568
PCT Pub. Date: Jan. 24, 2008

(65) Prior Publication Data
US 2009/0312588 A1  Dec. 17, 2009

(30) Foreign Application Priority Data
Jul. 17, 2006  (EP) .................................... 06117306

(51) Int. Cl.
*C07C 7/167*  (2006.01)

(52) U.S. Cl.
USPC ........... 585/262; 585/258; 585/259; 502/340; 502/341; 502/345; 502/346

(58) Field of Classification Search
USPC .......... 585/275, 250, 258, 259, 262; 502/300, 502/340, 341, 343, 346, 345
See application file for complete search history.

(56) References Cited

U.S. PATENT DOCUMENTS

| | | | | |
|---|---|---|---|---|
| 2,426,604 | A | * | 9/1947 | Frevel ............................. 585/262 |
| 3,549,719 | A | * | 12/1970 | Duyverman et al. ......... 423/219 |
| 3,637,529 | A | | 1/1972 | Van Beck et al. |
| 3,677,970 | A | | 7/1972 | Mertzweiller et al. |
| 3,701,739 | A | | 10/1972 | Bovarnick et al. |
| 3,754,050 | A | * | 8/1973 | Duyverman et al. ........... 95/144 |
| 3,912,789 | A | * | 10/1975 | Frevel et al. ................... 585/259 |
| 4,323,482 | A | | 4/1982 | Stiles et al. |
| 4,552,861 | A | | 11/1985 | Courty et al. |
| 4,593,148 | A | | 6/1986 | Johnson et al. |
| 4,705,906 | A | * | 11/1987 | Brophy et al. ................. 585/262 |
| 4,780,481 | A | | 10/1988 | Courty et al. |
| 4,835,132 | A | | 5/1989 | Sambrook |
| 4,871,710 | A | | 10/1989 | Denny et al. |
| 5,037,793 | A | | 8/1991 | Toussaint et al. |
| 5,453,412 | A | * | 9/1995 | Deckers et al. ............... 502/342 |
| 5,990,040 | A | * | 11/1999 | Hu et al. ........................ 502/342 |
| 6,204,416 | B1 | * | 3/2001 | Liedloff ........................ 568/361 |
| 6,238,640 | B1 | | 5/2001 | Eguchi et al. |
| 6,689,713 | B1 | * | 2/2004 | Zhao et al. .................... 502/345 |
| 6,706,885 | B2 | | 3/2004 | Yasuda et al. |
| 6,723,295 | B1 | | 4/2004 | Baier et al. |
| 6,987,152 | B1 | * | 1/2006 | Eisinger et al. ................. 526/77 |
| 2003/0036669 | A1 | | 2/2003 | Ryu et al. |
| 2004/0176653 | A1 | | 9/2004 | Vorberg et al. |
| 2005/0241478 | A1 | | 11/2005 | Junicke et al. |
| 2007/0117714 | A1 | | 5/2007 | Geyer et al. |

FOREIGN PATENT DOCUMENTS

| | | |
|---|---|---|
| BE | 748742 | 10/1970 |
| DE | 1929977 | 12/1969 |
| DE | 2012430 | 10/1971 |
| DE | 19848595 A1 | 4/2000 |
| EP | 0394842 A1 | 10/1990 |
| EP | 0434062 A1 | 6/1991 |
| EP | 0646410 A1 | 4/1995 |
| EP | 1331033 A8 | 7/2004 |
| WO | WO-95/23644 A1 | 9/1995 |
| WO | WO-96/14280 A1 | 5/1996 |
| WO | WO-02/068119 A1 | 9/2002 |
| WO | WO-02/094435 A1 | 11/2002 |
| WO | WO-2004/004901 A1 | 1/2004 |
| WO | WO-2004/022223 A2 | 3/2004 |
| WO | WO-2004/026800 A1 | 4/2004 |

OTHER PUBLICATIONS

Blanco, J., "Catalizadores en la industria: catalizadores heterogeneos. III. su aplicacion en procesos de hidrogenacion de hidrocarburos," Quimica E Industria, 1974, vol. 20, No. 9, pp. 604-606.

Carr, N.L., et al., "Remove arsine to protect catalyst," Hydrocarbon Processing, May 1985, pp. 100-102.

Derrien, M.L., "Selective hydrogenation applied to the refining of petrochemical raw materials produced by steam cracking," Stud. Suf. Sci. Catal., 1986, vol. 27, pp. 613-666.

Allmann, H.-M., et al., "Selective hydrogenations and purifications in the steamcracker downstream treatment," DGMK-Conference: Selective Hydrogenation and Dehydrogenation, Nov. 1993, pp. 1-29.

Allmann, H.-M., et al., "Selective hydrogenations and purifications in the steamcracker downstream treatment," DGMK-Conference: Selective Hydrogenation and Dehydrogenation, Nov. 1993, pp. 49-57.

* cited by examiner

*Primary Examiner* — In Suk Bullock
*Assistant Examiner* — Bradley Etherton
(74) *Attorney, Agent, or Firm* — Novak Druce Connolly Bove + Quigg LLP

(57) ABSTRACT

Unsaturated hydrocarbons are hydrogenated over catalysts which comprise copper and zinc and whose active composition, in unreduced form, consists essentially of from 10 to 95% by weight of copper oxide, calculated as copper(II) oxide (CuO), from 5 to 90% by weight of zinc oxide (ZnO), optionally from 0.1 to 50% by weight of zirconium dioxide ($ZrO_2$) and optionally from 0.1% by weight to 50% by weight of $Al_2O_3$, the proportions by weight adding up to 100% by weight.

14 Claims, No Drawings

PROCESS FOR HYDROGENATING UNSATURATED HYDROCARBONS IN THE PRESENCE OF CATALYSTS CONTAINING COPPER AND ZINC

CROSS-REFERENCE TO RELATED APPLICATIONS

This application is a national stage application (under 35 U.S.C. §371) of PCT/EP2007/056858, filed Jul. 5, 2007, which claims benefit of European application 06117306.8, filed Jul. 17, 2006.

BACKGROUND OF THE INVENTION

The present invention relates to a process for hydrogenating unsaturated hydrocarbons using catalysts comprising copper and zinc. In particular, the invention relates to a process for hydrogenating alkynes using catalysts comprising copper and zinc and especially to a process for hydrogenating alkynes in the presence of alkenes.

In refineries and petrochemical plants, hydrocarbon streams are obtained, stored and processed on a grand scale. In these hydrocarbon streams, unsaturated compounds, whose presence is known to lead to problems especially in processing and/or storage, or which are not the desired product of value, are frequently present, and are therefore undesired components of the corresponding hydrocarbon streams. General overviews of such problems in steamcrackers and typical solutions were given, for example, by H.-M. Allmann, Ch. Herion and P. Polanek in their presentation "Selective Hydrogenations and Purifications in the Steamcracker Downstream Treatment" at the DGMK Conference "Selective Hydrogenation and Dehydrogenation" on Nov. 11 and 12, 1993, in Kassel, Germany, whose manuscript was also published in Conference Report 9305 of the DGMK Deutsche Wissenschaftliche Gesellschaft für Erdöl, Erdgas und Kohle e. V., Hamburg, p. 1-30 (ISSN 0938-068X, ISBN 3-928164-61-9), and M. L. Derrien in: L. Cerveny (ed.), Stud. Surf. Sci. Catal., Vol. 27, p. 613-666, Elsevier, Amsterdam 1986.

Typically, the acetylene secondary component is undesired in C2 streams from steamcrackers, the propyne and allene secondary components are undesired in C3 streams, and the 1- and 2-butyne, 1,2-butadiene and vinylacetylene secondary components are undesired in C4 streams when 1,3-butadiene is to be obtained as the product of value and processed further, and also said secondary components and 1,3-butadiene itself in the cases in which 1-butene, 2-butene (in the cis- and/or the trans form) or isobutene are the desired products. In the processing of C5+ streams ("C5+": hydrocarbons having at least 5 carbon atoms, "pyrolysis gasoline"), di- and polyenes such as pentadiene and cyclopentadiene, alkynes and/or aromatics with unsaturated substituents such as phenylacetylene and styrene, are undesired when obtaining and processing aromatics or carburetor fuel.

In hydrocarbon streams which stem from an FCC cracker or a reformer instead of a steamcracker, analogous problems occur. A general overview of such problems, especially in C4- and C5+ streams from FCC crackers is given, for example, by J. P. Boitiaux, C. J. Cameron, J. Cosyns, F. Eschard and P. Sarrazin in their presentation "Selective Hydrogenation Catalysts and Processes: Bench to Industrial Scale" at the DGMK Conference "Selective Hydrogenation and Dehydrogenation" on Nov. 11 and 12, 1993, in Kassel, Germany, whose manuscript has also been published in Conference Report 9305 of the DGMK Deutsche Wissenschaftliche Gesellschaft für Erdöl, Erdgas und Kohle e. V., Hamburg, p. 49-57 (ISSN 0938-068X, ISBN 3-928164-61-9).

In general, unsaturated compounds with triple bonds (alkynes) and/or diunsaturated compounds (dienes) and/or other di- or polyunsaturated compounds (polyenes, allenes, alkylenes) and/or aromatic compounds having one or more unsaturated substituents (phenylalkenes and phenylalkynes) should therefore usually be removed from hydrocarbon streams in order to obtain the desired products, such as ethylene, propylene, 1-butene, isobutene, 1,3-butadiene, aromatics or carburetor fuel, in the required quality. Not every unsaturated compound is, however, an undesired component which should be removed from the hydrocarbon stream in question. For example, 1,3-butadiene, as already indicated above, is an undesired secondary component or the desired product of value depending on the case.

The removal of undesired unsaturated compounds from hydrocarbon streams comprising them is frequently done by selectively hydrogenating some or all of the undesired unsaturated compounds in the corresponding hydrocarbon stream, preferably by selective hydrogenation to undisruptive, more highly saturated compounds, and, in a particularly preferred manner, to components of the hydrocarbon streams which constitute the products of value. For example, acetylene is hydrogenated to ethylene in C2 streams, propyne and allene to propylene in C3 streams, butyne to butenes, vinylacetylene to 1,3-butadiene and/or 1,3-butadiene to butenes in C4 streams, and phenylacetylene and styrene to ethylbenzene, cyclopentadiene to cyclopentene and pentadiene to pentene in C5+ streams.

Typically, such compounds should be removed down to residual contents of a few ppm by weight. ("Over-")hydrogenation to compounds which are more highly saturated than the desired product of value and/or parallel hydrogenation of a product of value comprising one or more multiple bonds to the corresponding more highly saturated or completely saturated compound should, however, be avoided as far as possible owing to the associated loss of value. The selectivity of the hydrogenation of the undesired unsaturated compounds therefore has to be as high as possible. In addition, a sufficiently high activity of the catalyst and a long lifetime are generally desired. At the same time, the catalyst should as far as possible also not bring about any undesired side reactions; for example, catalysis of the isomerization of 1-butene to 2-butenes, with the exception of special cases, should as far as possible be avoided. Processes for selectively hydrogenating unsaturated compounds in hydrocarbon streams comprising them are known both in the form of liquid-phase hydrogenation or mixed gas/liquid phase hydrogenation, in trickle or liquid-phase mode, and also in the form of pure gas phase hydrogenation, various process technology measures for improving the selectivity having been published.

Typically, supported noble metal catalysts in which a noble metal is deposited on a catalyst support are used. Frequently, palladium is used as the noble metal; the support is generally a porous inorganic oxide, for example silica, aluminosilicate, titanium dioxide, zirconium dioxide, zinc aluminate, zinc titanate and/or mixtures of such supports, but aluminum oxide or silicon dioxide are usually used. In addition, promoters or other additives may be present. One disadvantage of noble metal catalysts ("noble metals" in this field of catalysis refer to silver, gold, rhodium, iridium, platinum and palladium) is their relatively high proneness to contaminations, known as "catalyst poisons", such as mercury, arsenic, sulfur, carbon monoxide and the like. A further disadvantage is the high cost of the noble metals. Although they can generally be recovered from the catalysts, a considerable amount of capital is tied up during their operation. Often, copper-comprising catalysts are therefore also used for hydrogenation, which are considerably more resistant toward catalyst poisons and considerably less expensive.

Copper-comprising catalysts, especially also copper- and zinc-comprising catalysts, are known. They are used predominantly as catalysts, absorbents or adsorbents for the removal of carbon monoxide from gas streams. WO 02/094435 A1 teaches a process for oxidatively removing CO from ethylene at temperatures in the range from 70 to 110° C. over catalysts comprising copper and zinc. U.S. Pat. No. 6,238,640 B1 describes a process for removing carbon monoxide from gas streams comprising hydrogen by reaction with steam and oxygen to give carbon dioxide and hydrogen in the presence of a catalyst which comprises copper oxide and aluminum oxide and at least one metal oxide from the group formed from zinc oxide, chromium oxide and magnesium oxide. DE-A 19 29 977 teaches catalysts comprising from 20 to 60 parts of CuO to 100 parts of ZnO and their use for removing CO from ethylene and propylene streams at a temperature in the range from 50 to 200° C., WO 2004/022223 A2 teaches an adsorption composition comprising copper, zinc, zirconium and optionally aluminum, and its use for removing CO from streams in the completely reduced state.

Catalysts comprising copper and zinc are also known for uses other than for the removal of CO from streams, U.S. Pat. No. 4,593,148 and U.S. Pat. No. 4,871,710 disclose processes for desulfurizing and dearsenating with Cu/Zn catalysts. WO 95/023644 A1 teaches a copper catalyst for the hydrogenation of carbon oxides, for example to methanol, or for the so-called shift reaction of carbon monoxide with water to give carbon dioxide and hydrogen, which, as well as dispersed copper, also comprises stabilizers such as silicon dioxide, aluminum oxide, chromium oxide, magnesium oxide and/or zinc oxide, and optionally also a support such as aluminum oxide, zirconium dioxide, magnesium oxide and/or silicon dioxide. DE 198 48 595 A1 discloses a catalyst for nitrous oxide decomposition of the general formula $M_xAl_2O_4$ in which M is Cu or a mixture of Cu and Zn and/or Mg, and which may comprise further dopants, especially Zr and/or La. U.S. Pat. No. 4,552,861 teaches a preparation process for catalysts which comprise Cu, Zn, Al and at least one element from the groups formed by the rare earths and zirconium, and also their use for methanol synthesis. The methanol catalysts disclosed in U.S. Pat. No. 4,780,481 comprise Cu, Zn and at least one alkali metal or alkaline earth metal, noble metals and/or rare earths, where Zn may be replaced partly by Zr. U.S. Pat. No. 4,835,132 describes CO shift catalysts which are obtained by calcination from a precursor of the formula $(Cu+Zn)_6Al_xR_y(CO_3)_{(x+y)/2}OH_{12+2(x+y)} \cdot nH_2O$ with layer structure, where R is La, Ce or Zr, x is at least 1 and at most 4, y is at least 0.01 and at most 1.5, and n is about 4.

U.S. Pat. No. 4,323,482 discloses methanization catalysts which comprise chromium and nickel and consist of an intimate mixture of a reducible metal oxide and at least one irreducible metal oxide, and which are activated by reduction at a temperature of from 550 to 1000° C. According to this document, this high temperature leads to fine metals and highly active catalysts. As an aside, mention is also made of the application of this catalyst preparation process to copper-comprising catalysts. U.S. Pat. No. 3,701,739 likewise teaches catalysts composed of a reducible oxide and at least one irreducible oxide, their preparation from an ammoniacal solution of hydroxides or carbonates, and their uses, including for hydrogenation. Mention is made, for instance, of catalysts composed of 30% CuO and 70% ZnO or CuO/ZnO/$Al_2O_3$ catalysts. These are used, for example, for the hydrogenation of acetone to isopropanol at 200° C. BE 748 7423 A describes the preparation of catalysts having a series of different active compositions on porous supports by precipitating onto the support with heating, and the use of such catalysts for the hydrogenation of amides at least 50° C. DE-A 20 12 430 discloses conversion catalysts composed of 30-55% by weight of CuO, 25-45% by weight of MgO, 2-30% by weight of $Al_2O_3$ and 0-30% by weight of $Cr_2O_3$ or ZnO. U.S. Pat. No. 5,990,040 describes conversion catalysts composed of 30-70% by weight of CuO, 20-90% by weight of ZnO, 0.1-20% by weight of an oxide of an element from group IVB, preferably Ti or Zr, 5-50% by weight of $Al_2O_3$ and 50-1000 ppm of an oxide of an element from group IA, which may, though, also be used for methanol synthesis, for purification and for hydrogenation. U.S. Pat. No. 6,706,885 B2 teaches a process for preparing 2,5-di(3'-aminoprop-1-ynyl)pyridines by Sonogashira coupling of 2,5-dihalopyridines with protected 3-aminopropynes over copper, zinc or zirconium catalysts.

As already mentioned, the use of copper-comprising catalysts for hydrogenations is also known. WO 96/014280 A1 teaches catalysts which comprise Cu, Zn and at least one compound of Al, Zr, Mg, of a rare earth metal and/or mixtures thereof, and their use for hydrogenating carboxylic esters. EP 434 062 A1 likewise teaches a process for hydrogenating carboxylic esters over a catalyst comprising Cu, Al and a metal selected from the group formed from Mg, Zn, Ti, Zr, Sn, Ni, Co and mixtures thereof. EP 394 842 A1 teaches catalysts comprising 20-75% by weight of NiO, 10-75% by weight of ZrO2 and 5-50% by weight of CuO for the hydrogenation of aliphatic unsaturated compounds such as butynediol at temperatures in the range from 40° C. to 200° C. and pressures of from 30 to 320 bar. EP 646 410 A1 discloses a process for obtaining alcohols by hydrogenation over a catalyst which comprises copper and zinc oxide and a further oxide as the active composition on a support coated with titanium oxide. The hydrogenation process is performed at a temperature of from 160° C. to 350° C. EP 1 331 033 A1 discloses a process for preparing spherical supported metal catalysts by dropletizing a mixture of a polysaccharide and at least one metal compound into a metal salt solution. A CuO catalyst on $SiO_2$ support prepared in this way is used for the hydrogenation of acetophenone at 80° C. and 20 bar of pressure. U.S. Pat. No. 3,677,970 mentions, as well as the sulfur-resistant nickel catalysts for the hydrogenation of hydrocarbons disclosed there, also a series of other catalysts which also include copper catalysts. WO 02/068119 A1 discloses a process for preparing catalysts comprising copper and at least one further element selected from the series of other elements including zinc by size-buildup granulation. These catalysts are used for the hydrogenation of functional organic compounds and for dehydrogenation. WO 2004/026800 A1 describes a process for preparing alcohols by hydrogenating aldehydes over sulfurized copper-zinc oxide catalysts at a temperature of from 240° C. to 280° C. and an (elevated) pressure of from 20 bar to 400 bar.

WO 2004/004901 A1 teaches a process for hydrogenating C4-acetylenes in a liquid hydrocarbon stream over coated catalysts comprising copper on zeolitic support materials at temperatures in the range of from 20 to 80° C. (in the examples, temperatures of 60° C. are used) and pressures of 15 and 50 bar. N. L. Carr, D. L. Stahlfeld and H. G. Robertson, in Hydrocarbon Processing, May 1985, p. 100-102, report copper-comprising absorption compositions for removing arsenic from olefin streams. The hydrogenation of the olefins is in this case a side reaction which can be suppressed by avoiding temperatures above of 250° F. (corresponding to 121° C.). J. Blanco, in Quimica e Industria 20 (1974) 604-606, reports that hydrocarbons are hydrogenated over copper catalysts only at temperatures of at least 300° C. and pressures around 300 bar.

One disadvantage of common hydrogenation catalysts with copper as the hydrogenation-active metal is accordingly that relatively high hydrogenation temperatures are needed. However, some streams already exhibit decomposition phenomena at these temperatures, for example, in typical propylene streams—which always also comprise traces of oxygen—oxygenates are formed even from 50° C. Such oxygenates can act as catalyst poisons in downstream processes, for instance preparation of polypropylene over metallocene catalysts, and are therefore extremely undesirable.

The requirements on processes for the selective hydrogenation of undesired unsaturated compounds are rising constantly. It is therefore an object of the invention to find an improved process for selectively hydrogenating unsaturated compounds, especially a process which avoids the formation of by-products such as oxygenates. At the same time, activity and selectivity of the catalysts should be high.

BRIEF SUMMARY OF THE INVENTION

Accordingly, a process has been found for hydrogenating unsaturated hydrocarbons over catalysts comprising copper and zinc, which comprises using a catalyst whose active composition, in unreduced form, consists essentially of from 10 to 95% by weight of copper oxide, calculated as copper(II) oxide (CuO), from 5 to 90% by weight of zinc oxide (ZnO), optionally from 0.1 to 50% by weight of zirconium dioxide ($ZrO_2$) and optionally from 0.1% by weight to 50% by weight of $Al_2O_3$, the proportions by weight adding up to 100% by weight.

DETAILED DESCRIPTION OF THE INVENTION

The process according to the invention makes it possible to hydrogenate unsaturated hydrocarbons in an economically viable manner under mild conditions. The formation of oxygenates is avoided, as is the high capital tie-up in the case of noble metal catalysts. Undesired overhydrogenation is avoided; the process is suitable for the selective hydrogenation of alkynes in alkene streams. The catalyst is resistant to poisoning.

The active composition of the catalyst to be used in accordance with the invention comprises, in unreduced form, copper oxides and zinc oxides, and also optionally zirconium oxides and aluminum oxides. Under reaction conditions, i.e. in the presence of reducing compounds such as hydrogen, copper is present at least partly, but generally completely, in the form of metallic copper. In the preparation of the catalyst, it is typically obtained in the form of Cu(I) oxides and Cu(II) oxides; this is also the form of the catalyst which can be stored and transported without risk.

In pure form, the active composition of the catalysts to be used in accordance with the invention generally comprises copper in an amount which, calculated as CuO, is at least 10% by weight, preferably at least 20% by weight and more preferably at least 30% by weight, and generally at most 95% by weight, preferably at most 85% by weight and more preferably at most 80% by weight of copper oxide CuO, based in each case on the total amount of the active composition. In pure form, it generally comprises zinc oxide ZnO in an amount of at least 5% by weight, preferably at least 10% by weight and more preferably at least 15% by weight, and generally at most 90% by weight, preferably at most 80% by weight and more preferably at most 70% by weight, based in each case on the total amount of the active composition. In pure form, it further optionally comprises zirconium dioxide $ZrO_2$. When this is present, its proportion is generally at least 0.1% by weight, preferably at least 3% by weight and more preferably at least 5% by weight, and generally at most 50% by weight, preferably at most 40% by weight and more preferably at most 30% by weight, based in each case on the total amount of the active composition. It further optionally comprises aluminum oxide $Al_2O_3$. When this is present, its proportion is at least 0.1% by weight, preferably at least 3% by weight and more preferably at least 50% by weight, and generally at most 50% by weight, preferably at most 40% by weight and more preferably at most 30% by weight, based in each case on the total amount of the active composition. In the context of this invention, "pure form" means that, apart from the copper (oxide), zinc oxide, zirconium dioxide and aluminum oxide fractions, no further constituents are present apart from insignificant constituents which are, for example, entrained from the manufacture, such as residues of starting materials and reagents, assistants for shaping and the like. "Pure form" thus means that the active composition consists essentially of the components mentioned.

The percentages of the components of the active composition always add up to 100% by weight.

Very suitable active compositions consist, in pure form, for example of approx. 40% by weight of CuO, approx. 40% by weight of ZnO and approx. 20% by weight of $Al_2O_3$; of approx. 70% by weight of CuO, approx. 20% by weight of ZnO and approx. 10% by weight of $ZrO_2$, or of approx. 70% by weight of CuO, approx. 25% by weight of ZnO and approx. 5% by weight of $Al_2O_3$, their proportions adding up to 100% by weight.

The active composition can, but need not necessarily, be applied to an inert support. Suitable inert supports are the known catalyst supports, for example aluminum oxide, silicon dioxide, zirconium dioxide, aluminosilicates, clays, zeolites, kieselguhr and the like. It is equally possible to use further known assistants for the processing of solids such as catalysts. Preference is given to using the active composition without support, i.e. active composition and catalyst are preferably identical.

Such catalysts are common commercial materials. Processes for preparing such catalysts are known. A convenient and preferred process comprises the following process steps in the sequence mentioned:

a) Preparation of a solution or suspension of the components of the catalyst and/or starting compounds thereof;
b) precipitating a solid from this solution by adding a base, optionally with mixing of the precipitation product with further components of the catalyst and/or of starting compounds thereof;
C) removing and drying the solid;
d) optionally calcining the solid;
e) shaping the solid to tablets; and
f) optionally calcining the tablets;
at least one of the two calcination steps d) or f) being performed.

In the first process step, step a), a solution of the components of the catalyst is prepared in a customary manner, for example by dissolution in an acid such as nitric acid. Optionally, instead of the components of the catalyst, their starting compounds are also used, for example the nitrates, carbonates, hydroxycarbonates of the metals, are dissolved in an aqueous solution which may also be acidic, for example a nitric acid solution. The ratio of the salts in solution is calculated stoichiometrically and adjusted according to the desired end composition of the catalyst. It is equally possible to add components in insoluble form, for example aluminum oxide, as fine particles, and thus to obtain and to use a suspension in which some components are dissolved and others are suspended.

From this solution, a solid is precipitated in step b) as a precursor of the catalyst. This is done in a customary manner, preferably by increasing the pH of the solution by adding a base, for instance by adding sodium hydroxide solution or sodium carbonate solution.

The solid precipitation product formed is generally removed from the supernatant solution before the drying in step c), for instance by filtration or decanting, and washed with water to free it of soluble constituents such as sodium nitrate. It is equally possible to precipitate only some components of the catalyst or their precursors in this way, and to mix the solid precipitation product with further, for example insoluble, components, for instance aluminum oxide. It is possible in principle to do this by mixing dried powders, but the mixing is preferably effected as a suspension before removal and drying of the precipitation product.

The precipitation product (if appropriate mixed with further insoluble components) is then normally dried with customary drying methods before the further processing. In general, a treatment at slightly elevated temperature is sufficient for this purpose, for instance about 80° C., preferably at least 100° C. and more preferably at least 120° C., over a period of from 10 min to 12 hours, preferably from 20 min to 6 hours and more preferably from 30 min to 2 hours. It is also possible and particularly convenient to convert the product of the precipitation directly—a certain alkali metal content, for example sodium content, of the catalyst is generally not disruptive—or after washing by spray drying, to a dry powder suitable for further processing.

After the drying, the precipitated and dried precursor of the catalyst is optionally subjected to the calcination step d). The calcination temperature employed is generally at least 250° C., preferably at least 300° C. and more preferably at least 350° C., and generally at most 500° C., preferably at most 450° C. and more preferably at most 410° C. The calcination time is generally at least 10 minutes, preferably at least 20 minutes and more preferably at least 30 minutes, and generally at most 12 hours, preferably at most 6 hours and more preferably at most 4 hours. The drying step c) and the calcination step d) may merge directly into one another.

After the drying step c) or the calcination step d), the catalyst or its precursor is processed in shaping step e) by customary shaping processes such as extruding, tableting or pelletizing to moldings such as strands or extrudates, tablets or pellets, including spherical pellets.

After the shaping step, the catalyst (i.e. to be more precise its precursor) is optionally subjected to a calcination step f). The calcination temperature employed here is generally at least 300° C., preferably at least 350° C. and more preferably at least 400° C., in particular at least 450° C. and generally at most 700° C., preferably at most 650° C. and more preferably at most 600° C., in particular at most 580° C. The calcination time is generally at least 30 minutes, preferably at least 60 minutes, and generally at most 10 hours, preferably at most 3 hours and more preferably at most 2 hours, in particular at most 90 minutes. In a particularly preferred embodiment, the temperature is increased slowly within the range mentioned over the calcination time.

During the calcination steps, the catalyst precursor is converted to the actual catalyst and, among other parameters, the BET surface area and the pore volume of the catalyst are adjusted as usual, the BET surface area and the pore volume being known to fall with increasing calcination time and calcination temperature.

At least one of the two calcination steps is performed.

Preference is given to calcining overall for at least a sufficiently long period that the content in the catalyst of carbonate (calculated as $CO_3^{2-}$) is at most 10% by weight, based on the total weight of the calcination product, and its BET surface area has a value in the range of at least 10 $m^2/g$, preferably at least 30 $m^2/g$ and, in a particularly preferred form, at least 40 $m^2/g$, in particular at least 50 $m^2/g$, and generally at most 100 $m^2/g$, preferably at most 90 $m^2/g$ and, in particularly preferred form, at most 80 $m^2/g$, in particular at most 75 $m^2/g$. The pore volume of the catalyst, measured as the water uptake, is adjusted in the calcination to a value of at least 0.05 ml/g. These values are preferred for the catalyst to be used in the process according to the invention.

In the preparation of the catalyst, it will be appreciated that it is possible to use known assistants, for example pore formers or tableting assistants which decompose in the course of calcination.

The catalyst may also, as mentioned above, be deposited on a support. This is done by customary impregnation processes or precipitation processes. A precipitation process is known to be a precipitation process in the presence of a support or of a support precursor. To perform a precipitation process, preference is given to adding a support or support precursor in the precipitation process of the solution prepared in step a) detailed above. If the support is already present in the form of preshaped finishing moldings, i.e. a pure impregnation process is performed, the shaping step e) is dispensed with, otherwise the support is also formed in the course of the processing of the precursor of the catalyst by precipitation, drying, calcination and shaping.

A preferred precipitation process for preparing the catalyst is performed with preshaped supports and comprises the following process steps in the sequence mentioned:
a) preparing a solution of the components of the catalyst and/or of soluble starting compounds thereof;
b) impregnating a preshaped support with this solution;
c) drying the impregnated support; and
d) calcining the impregnated and dried support.

Process step a) of this impregnation process is carried out like the above-described step a) of the precipitation process. In step b), a preshaped support is impregnated with the solution. The preshaped support has a shape selected corresponding to the intended use, for example strands or extrudates, tablets or pellets, including spherical pellets. The impregnation is performed either with supernatant solution or as an impregnation with the amount of solution corresponding to the pore volume of the support ("incipient wetness"). After the impregnation, the impregnated support is dried and calcined in steps c) and d) like the precipitation product in the precipitation process. Since a preshaped support is used, the shaping step is dispensed with.

After the calcination, the catalyst is present in oxidic form, i.e. the copper present therein is predominantly or exclusively in the form of copper oxides. For the hydrogenation, the catalyst has to be reduced, i.e. the copper has to be present predominantly or exclusively in the metallic state. The reduction is effected by treating the oxidic catalyst present after calcination with a reducing agent. This can in principle be done by any reducing agent which can reduce copper from the I or II oxidation states to the 0 oxidation state. The precise reaction conditions to be used are dependent upon the catalyst, its precise state before reduction and upon the reducing agent used, and can be determined easily in a few routine experiments. Processes for reducing copper catalysts are known.

The reduction can be effected with liquid or dissolved reducing agents; in this case, the reduction has to be followed by drying. It is therefore very much more convenient to reduce with a gaseous reducing agent, in particular to reduce with hydrogen by passing over a hydrogen-comprising gas. The temperature to be employed here is generally at least 80° C., preferably at least 100° C. and more preferably at least 120° C., and generally at most 180° C., preferably at most 160° C. and more preferably at most 140° C. A suitable temperature is, for example, approx. 130° C. The reduction is exothermic. The amount of reducing agent added should be adjusted so as not to leave the selected temperature window. The profile of the activation can be monitored with reference to the temperature measured in the bed of the adsorbent ("temperature-programmed reduction, TPR").

A preferred method for reduction is, after a drying performed under a nitrogen stream, to adjust the desired reduction temperature and to add a small amount of hydrogen to the nitrogen stream. At the start, a suitable gas mixture comprises, for example, at least 0.1% by volume of hydrogen in nitrogen, preferably at least 0.5% by volume and more preferably at least 1% by volume, and at most 10% by volume, preferably at most 8% by volume and more preferably at most 5% by volume. A suitable value is, for example, 2% by volume. This starting concentration is either retained or increased in order to attain and to keep the desired temperature window. The reduction is complete when, in spite of constant or rising level of the reducing agent, the temperature in the bed of the composition declines. A typical reduction time is generally at least 1 hour, preferably at least 10 hours and more preferably at least 15 hours, and generally at most 100 hours, preferably at most 50 hours and more preferably at most 30 hours.

The drying, if required, is achieved by heating the catalyst to a temperature of generally at least 100° C., preferably at least 150° C. and more preferably at least 180° C., and generally at most 300° C., preferably at most 250° C. and more preferably at most 220° C. A suitable drying temperature is, for example, approx. 200° C. The precursor is kept at the drying temperature until only residues of adhering moisture which are no longer troublesome are present; this is generally the case for a drying time of at least 10 minutes, preferably at least 30 minutes and more preferably at least 1 hour, and generally at most 100 hours, preferably at most 10 hours and more preferably at most 4 hours. The drying preferably takes place in a gas stream in order to transport the moisture away from the bed. To this end, for example, dry air can be used, but particular preference is given to flowing an inert gas through the bed; suitable gases here are in particular nitrogen or argon.

Conveniently, the drying and the reduction are performed before the catalyst is used for the hydrogenation in the hydrogenation reactor, since transport and storage of the catalyst in the reduced state entail particular safety measures and are difficult. However, the catalyst can also be reduced outside the hydrogenation reactor, for instance by the catalyst manufacturer, and be passivated again by partial reoxidation by customary processes in order to simplify transport and storage. Before the use for the hydrogenation, it should then be completely reduced again. These measures are common and generally known for copper catalysts.

The hydrogenation process according to the invention is notable by the use of the above-described catalyst. The hydrogenation process according to the invention using the catalyst described is generally performed just like the known heterogeneously catalyzed hydrogenation processes which serve the same purposes. They may be performed as heterogeneously catalyzed gas phase processes in which both the hydrocarbon stream and the hydrogenating hydrogen are present in the gas phase, or as a heterogeneously catalyzed gas/liquid phase process in which the hydrocarbon stream is present at least partly in the liquid phase and hydrogen is present in the gas phase and/or in dissolved form in the liquid phase. The parameters to be adjusted, such as throughput of hydrocarbon stream expressed as superficial velocity in the unit $[m3/m3*h^{-1}]$, based on the catalyst volume, temperature and pressure, are selected analogously to those of known processes. The temperature in the process according to the invention is generally at least −50° C., preferably at least −10° C. and, in particularly preferred form, at least 0° C., and generally at most 250° C., preferably at most 100° C. and, in particularly preferred form, at most 50° C. The pressure is generally at least 0.01 bar abs., preferably at least 0.8 bar abs. and, in particularly preferred form, at least 1 bar abs., and generally at most 750 bar abs., preferably at most 325 bar abs. and, in particularly preferred form, at most 40 bar abs.

The amount of the hydrogen used, based on the amount of the hydrocarbon stream fed, is dependent upon the content in the hydrocarbon stream of undesired unsaturated compounds and their type. In general, the hydrogen is added in an amount of from 0.8 up to 5 times the amount required stoichiometrically for complete hydrogen conversion in a reactor pass, preferably in the range of from 0.95 to 2 times this amount. The hydrogenation of triple bonds normally proceeds more rapidly than the conjugated double bonds, and this in turn more rapidly than the unconjugated double bonds. This allows appropriate control of the process with regard to the amount of hydrogen added. In special cases, for example when high isomerization of 1-butene to cis- or trans-2-butene is desired, it is also known that a relatively high hydrogen excess, for example a ten fold hydrogen excess, can be used. The hydrogen may comprise inert gases, for example noble gases such as helium, neon or argon, other inert gases such as nitrogen, carbon dioxide and/or lower alkanes, for instance methane, ethane, propane and/or butane. Such inert gases in the hydrogen are present preferably in a concentration of less than 30% by volume. Moderation of the catalyst by deliberate carbon monoxide addition is generally not required.

The process can be performed in one reactor or in a plurality of parallel or series-connected reactors, in each case in single pass or in circulation mode. When the process is performed in the gas/liquid phase, the hydrocarbon stream, after passing through one reactor, is typically freed of gases in a separator, and some of the liquid obtained is recycled into the reactor. The ratio between recycled hydrocarbon stream and hydrocarbon stream fed for the first time into the reactor, known as the reflux ratio, is adjusted such that the desired conversion is achieved under the other reaction conditions, such as pressure, temperature, throughput and amount of hydrogen.

The purpose of using the process according to the invention is, for instance, the hydrogenation of alkynes to alkadienes, of alkynes, alkynenes and alkadienes to alkenes, of phenylalkynes to phenylalkenes and/or of phenylalkenes to phenylalkanes.

Examples of applications of the process according to the invention are those:

for the selective hydrogenation of acetylene in C2 streams to ethylene with minimal formation of ethane (this embodiment of the process is referred to hereinafter as "process A" for simplification), for the selective hydrogenation of propyne and/or propadiene in C3 streams to give propylene with minimal formation of propane ("process B"), for the selective hydrogenation of 1-butyne, 2-butyne, 1,2-butadiene and/or vinylacetylene in C4 streams to give 1,3-butadiene, 1-butene, cis- and/or trans-2-butene ("process C"), for the selective hydrogenation of 1-butyne, 2-butyne, 1,2-butadiene, 1,3-butadiene and/or vinylacetylene in C4 streams to give 1-butene, cis- and/or trans-2-butene, in butadiene-rich C4 streams ("crude C4 cut") or low-butadiene C4 streams ("raffinate I") ("process D"), and for the selective hydrogenation of unsaturated compounds and/or unsaturated substituents of aromatic compounds in C5+ streams to more highly saturated compounds and/or aromatic compounds having more highly saturated substituents with minimal hydrogenation of the aromatic rings ("process E"), in each case using the above-described catalysts.

Process A is performed typically as a gas phase process with a superficial velocity of the gaseous C2 stream of from 500 $m^3/m^3*h$, based on the catalyst volume, to 10 000 $m^3/m^3*h$ at a temperature of from 0° C. to 110° C. and a pressure of from 0.01 bar to 50 bar, one mole of hydrogen being added per mole of acetylene in the C2 stream.

Process B is performed typically as a gas phase process or as a gas/liquid phase process with a superficial velocity of the liquid C3 stream of from 1 $m^3/m^3*h$, based on the catalyst volume, to 50 $m^3/m^3*h$ at a temperature of from 0° to 50° C. and a pressure of from 0.01 bar to 50 bar, from one to two moles of hydrogen being added per mole of propyne and propadiene in the C3 stream.

Process C is performed typically as a gas/liquid phase process with a superficial velocity of the liquid C4 stream of from 1 $m^3/m^3*h$, based on the catalyst volume, to 50 $m^3/m^3*h$ at a temperature of from 0° C. to 180° C. and a pressure of from 2 bar to 50 bar, from one to two moles of hydrogen being added per mole of butyne, 1,2-butadiene and vinylacetylene in the C4 stream. Process C can be used, for example, as a selective "front-end vinylacetylene hydrogenation" before a butadiene extraction.

Process D is performed typically as a one- or two-stage gas/liquid phase process with a superficial velocity of the liquid C4 stream in the range of from 0.1 $m^3/m^3*h$, based on the catalyst volume, to 60 $m^3/m^3*h$, preferably of from 1 $m^3/m^3*h$ to 50 $m^3/m^3*h$, at a reactor entrance temperature in the range from 20° C. to 90° C., preferably from 20° C. to 70° C., and a pressure in the range of from 5 bar to 50 bar, preferably from 10 bar to 30 bar, one mole of hydrogen being added per mole of butyne, butadiene and vinylacetylene in the C4 stream. For example, the process is performed in two stages, in which case the butadiene content, which, in typical C4 streams from steamcrackers, is in the range from 20% by weight to 80% by weight, based on the overall stream, is reduced in the first stage down to a content in the range of from 0.1% by weight to 20% by weight, and, in the second stage, down to the desired residual content in the range from a few ppm by weight to about 1% by weight. It is equally possible to divide the overall reaction between more than two reactors, for example three or four. The individual reaction stages may be operated with partial recycling of the hydrocarbon stream; the reflux ratio is typically in the range from 0 to 30. When process D is performed, isobutene remains essentially unchanged and can be removed from the C4 stream by known methods before or after the performance of process D. Process D can be used, for example, as a butadiene hydrogenation in the C4 stream (when butadiene is not to be obtained as the product of value) or a selective "tail-end vinylacetylene hydrogenation" after the butadiene extraction from the C4 stream.

Process E is performed preferably as a gas/liquid phase process with a superficial velocity of the liquid C5+ stream of from 0.5 $m^3/m^3*h$, based on the catalyst volume, to 30 $m^3/m^3*h$ at a temperature of from 0° C. to 180° C. and a pressure of from 2 bar to 50 bar, from one to two moles of hydrogen being added per mole of compounds to be hydrogenated in the C5+ stream. Process E can be used, for example, as a selective pyrolysis gasoline hydrogenation, as a selective hydrogenation of olefins in reformate streams or coking oven condensates, for the hydrogenation of phenylacetylene to styrene or for the hydrogenation of styrene to ethylbenzene.

EXAMPLES

Examples 1 to 4

Preparation of Catalysts A-D

A heatable 10 l precipitation vessel equipped with a stirrer was initially charged in each case with 1.2 l of water and heated to 70° C. Subsequently, metal nitrate solutions in nitric acid were in each case metered in with stirring in the amounts needed to achieve the composition, specified below in Table 1, of the catalysts A-D thus prepared. At the same time, a 20% by weight sodium carbonate solution was metered in such that a pH of 6.5 was maintained in the precipitation vessel. The suspensions formed were stirred at 70° C. and pH 6.5 for 120 minutes, then filtered off and washed with cold water to free them of nitrate (<25 ppm of nitrate in the effluent). The filtercakes were dried, then calcined at 300° C. over 4 hours and then tableted.

In the case of catalysts A and B, another calcination step was performed after tableting.

TABLE 1

| Composition, in each case in % by weight, of the catalysts of Examples 1-4 | | | | | |
|---|---|---|---|---|---|
| Example No. | Catalyst | CuO | ZnO | $Al_2O_3$ | $ZrO_2$ |
| 1 | A | 40 | 40 | 20 | — |
| 2 | B | 70 | 20 | — | 10 |
| 3 | C | 40 | 40 | 20 | — |
| 4 | D | 70 | 25 | 5 | — |

Examples 5 to 8

Hydrogenation of Acetylene in a C2 Stream

Samples of the tablets obtained in Example 1 were reduced with hydrogen and then contacted in a tubular reactor with a C2 stream (ethylene, mixed with the proportions of hydrogen and acetylene specified in Table 2 below) at a superficial velocity (GHSV) of 2300 $h^{-1}$ and the temperature specified in the table. The pressure set was ambient pressure, i.e., upstream of the reactor, only the pressure needed to overcome the pressure drop of the apparatus was set. The proportions of hydrogen and acetylene measured downstream of the reactor are specified in Table 2 below.

TABLE 2

Hydrogenation of acetylene

| Example No. | Catalyst | Temp. [° C.] | Upstream of reactor [ppm by volume] | | Downstream of reactor [ppm by volume] | |
|---|---|---|---|---|---|---|
| | | | $H_2$ | $C_2H_2$ | $H_2$ | $C_2H_2$ |
| 5 | A | 100 | 580 | 376 | <10 | <2 |
| 6 | B | 25 | 959 | 620 | 6 | <2 |
| 7 | C | 25 | 741 | 705 | 50 | <2 |
| 8 | D | 25 | 638 | 681 | 37 | 7 |

Examples 5-8 show that acetylene in a C2 stream can be removed virtually completely at very low temperatures by the process according to the invention.

Examples 9-11

Hydrogenation of Propyne

Samples of the tablets obtained in Example 1 were reduced with hydrogen and then contacted in an autoclave at a pressure of 20 bar and 25° C. over 2 hours with liquid propene ($C_3H_6$) which had been admixed with 120 ppm by weight of propyne ($C_3H_4$) and 450 ppm by weight of hydrogen. The propene further comprised 300 ppm of propane ($C_3H_8$).

The proportions of hydrogen, propane and propyne which were measured subsequently are reported in Table 3 below.

TABLE 3

Hydrogenation of propyne in propene

| Example No. | Catalyst | After reaction [ppm by weight] | | |
|---|---|---|---|---|
| | | $H_2$ | $C_3H_8$ | $C_3H_4$ |
| 9 | B | 310 | 330 | <2 |
| 10 | C | 382 | 310 | <2 |
| 11 | D | 340 | 510 | <2 |

Examples 9-11 show that the virtually complete removal of propyne in C3 streams is possible in a highly selective manner at comparatively low temperatures by the process according to the invention.

The invention claimed is:

1. A process for hydrogenating alkynes in C2 or C3 streams which comprises hydrogenating the alkynes over the catalyst whose active composition, in unreduced form, consists essentially of
   from 10 to 95% by weight of copper oxide, calculated as copper(II) oxide (CuO),
   from 5 to 90% by weight of zinc oxide (ZnO),
   from 0.1 to 50% by weight of zirconium dioxide ($ZrO_2$) and
   optionally from 0.1% by weight to 50% by weight of $Al_2O_3$,
   the proportions by weight adding up to 100% by weight, wherein hydrogenation is effected at a temperature of at most 50° C.

2. The process according to claim 1, wherein the catalyst in unreduced form, consists essentially of
   from 20 to 85% by weight of copper oxide, calculated as copper(II) oxide (CuO),
   from 10 to 80% by weight of zinc oxide (ZnO),
   from 3 to 40% by weight of zirconium dioxide ($ZrO_2$) and
   optionally from 3% by weight to 40% by weight of $Al_2O_3$,
   the proportions by weight adding up to 100% by weight.

3. The process according to claim 2, wherein acetylene in an ethylene stream is hydrogenated.

4. The process according to claim 2, wherein propyne and allene in a propylene stream are hydrogenated.

5. The process according to claim 1, wherein the catalyst in unreduced form, consists essentially of
   from 30 to 80% by weight of copper oxide, calculated as copper(II) oxide (CuO),
   from 15 to 70% by weight of zinc oxide (ZnO),
   from 5 to 30% by weight of zirconium dioxide ($ZrO_2$) and
   optionally from 3% by weight to 30% by weight of $Al_2O_3$,
   the proportions by weight adding up to 100% by weight.

6. The process according to claim 5, wherein acetylene in an ethylene stream is hydrogenated.

7. The process according to claim 5, wherein propyne and allene in a propylene stream are hydrogenated.

8. The process according to claim 1, wherein acetylene in an ethylene stream is hydrogenated.

9. The process according to claim 1, wherein propyne and allene in a propylene stream are hydrogenated.

10. The process according to claim 1, wherein hydrogenation is effected at a temperature of at most 25° C.

11. The process according to claim 1, wherein $Al_2O_3$ is present in the catalyst.

12. The process according to claim 1, wherein the catalyst in unreduced form, consists essentially of
    from 40 to 70% by weight of copper oxide, calculated as copper(II) oxide (CuO),
    from 20 to 40% by weight of zinc oxide (ZnO),
    from 5 to 30% by weight of zirconium dioxide ($ZrO_2$) and
    optionally from 5% by weight to 20% by weight of $Al_2O_3$, and
    the proportions by weight adding up to 100% by weight.

13. The process according to claim 12, wherein $Al_2O_3$ is present in the catalyst.

14. The process according to claim 1, wherein the copper oxide is present in a weight percent equal to or greater than the weight percent of the zinc oxide.

* * * * *